United States Patent [19]

Davis-Hoover et al.

[11] Patent Number: 5,858,763
[45] Date of Patent: Jan. 12, 1999

[54] THERMOPHILIC METHANOTROPHS FOR HIGH TEMPERATURE OXIDATIONS

[75] Inventors: Wendy J. Davis-Hoover, West Chester; Stephen J. Vesper, Kettering, both of Ohio

[73] Assignees: The United States of America as represented by the Administrator of the Environmental Protection Agency, Washington, D.C.; by said Wendy J. Davis-Hoover; University of Cincinnati, Ohio; by said Stephen J. Vesper

[21] Appl. No.: 847,507

[22] Filed: Apr. 25, 1997

Related U.S. Application Data

[60] Provisional application No. 60/017,031 Apr. 26, 1996.
[51] Int. Cl.$^6$ .............................. C12N 1/20; C12N 9/00; C12N 9/24; C12P 1/04
[52] U.S. Cl. ............... 435/252.4; 435/42; 435/262.5; 435/183; 435/194; 435/198; 435/200
[58] Field of Search ................... 435/262.5, 252.4, 435/42, 183, 194, 198, 200

[56] References Cited

U.S. PATENT DOCUMENTS

| | | | |
|---|---|---|---|
| 5,316,940 | 5/1994 | Georgiou et al. | 435/262.5 |
| 5,384,048 | 1/1995 | Hazen et al. | 435/262.5 |
| 5,441,887 | 8/1995 | Hanson et al. | 435/262.5 |
| 5,518,919 | 5/1996 | Tyndall | 435/262.5 |

OTHER PUBLICATIONS

Derwent WPIL Abstract 96–015256/02 Ebara Sogo Kenkyusho KK JP07289247 (Nov. 7, 1995).

*Primary Examiner*—Herbert J. Lilling
*Attorney, Agent, or Firm*—Glenna Hendricks; Alan Ehrlich

[57] ABSTRACT

The invention is a consortium of thermophilic methanotrophic organisms in culture medium containing said consortium reproduced at temperatures of 50° C. to 80° C., said consortium being comprised primarily of ovoid or rod-shaped organisms. The consortium can be instilled into soil or water to degrade pollutants, especially hydrocarbons and substituted hydrocarbons.

18 Claims, No Drawings

THERMOPHILIC METHANOTROPHS FOR HIGH TEMPERATURE OXIDATIONS

This application relates back to and is a continuation of Provisional Patent Application 60/017,031 filed Apr. 26, 1996.

FIELD OF THE INVENTION

This application relates to a consortium of thermophilic bacteria which are methanotrophs, organisms which produce methane monooxygenase enzymes. The consortium has been produced in the presence of methane and functions at temperatures above 50° C. The consortium of organisms can be used to degrade organic contaminants and for production of chemicals, especially stereo-specific isomers.

BACKGROUND OF THE INVENTION

A group of aerobic microorganisms known as methanotrophs have previously been used to degrade organic contaminants. This group of organisms produces monooxygenases which oxidize methane and, in the absence of methane, after the enzyme has been produced, will incidently oxidize other compounds such as halogenated hydrocarbons, alkanes, alcohols, etc.

One of the more prevalent contaminants which have been degraded by co-metabolisms using methanotrophs is trichloroethylene. (TCE), an organic solvent that is used widely for metal processing, dry cleaning and in production of coatings. Because of leaks, spills and dumping, TCE is frequently found in subsurface soil environments. TCE is one of the most commonly found pollutants at hazardous waste sites. TCE and other chlorinated hydrocarbons are frequent pollutants of ground water. Most attempts to remediate the contamination of soils and aquifers have involved use of pump or vacuum means to bring the contaminated material to the surface for treatment. These means have resulted in limited removal of contaminants. The prior art practices are expensive and generally have no end-point to their operations. Limitations relating to hydraulic conductivity, soil matrix, desorption and residual saturation or pockets of contaminants present real problems when practicing the prior art methods of remediation.

An electrokinetic process developed by Casagrande has been used to dewater soils. This process has been used to remove contaminants from soil and aquifers. The process utilizes a direct current (DC electric field to induce the movement of water and dissolved ions as a means of transporting the contaminant. The method is beneficial only when contaminants are reasonably soluble in water (for example, benzene, toluene, xylene, phenol and chlorinated solvents). Moreover, the electrokinetic process results in transport, not degradation, of the contaminants. Therefore, electrokinetic application to soil provides only an incomplete solution to problems of contamination of soil and water. Ho has applied the electrokinetic methods to movement and capture of p-nitrophenol (PNP) with granular activated carbon (GAC) filled cassettes. However, the problems relating to removing and disposing of the contaminated cassettes remain unsolved.

SUMMARY OF THE INVENTION

The invention is a consortium of thermophilic methanotrophic organisms in culture medium containing said consortium reproduced at temperatures of 50° C. to 80° C., said consortium being comprised primarily of ovoid or rod-shaped organisms. The consortium can be instilled into soil or water to degrade pollutants, especially hydrocarbons and substituted hydrocarbons.

DETAILED DESCRIPTION OF THE INVENTION

This invention provides consortia of thermophilic methanotrophs for use in degradation of pollutants, especially pollutants found in soil and ground water. The consortia will grow and metabolize pollutants at temperatures of over 50° C. The consortia of the invention can be used in conjunction with electrokinetic means to alleviate environmental pollution, particularly pollution of ground water and soil. The pollutants are drawn to the remediation zone (RZ) containing the consortium using hydraulic transfer means such as electrokinetics. The consortium has been deposited in the American Type Culture Collection in Rockville, Md., U.S.A and has been assigned the ATCC number 55945.

The consortia of the invention may also be used in industrial fermentation processes of the prior art. These processes include pulping and recycling of cellulose-containing materials to produce intermediates and end products such as alcohols, the improvement being that the processes can be run at higher temperatures. These also include production of alcohols from alkanes and the formation of epoxides and useful intermediates. The consortium of the invention may also be used for degradation of alcohols such as methanol.

MATERIALS AND METHODS

Thermophilic Methanotroph Consortium Development

A consortium of thermophilic methanotrophs was developed from soil and water samples collected at Yellowstone National Park. The samples from which the consortium was developed came primarily from the Artist Paint Pot area and the Calcite Springs. Calcite Springs is one of only two natural oil seeps in the park and is associated with a hot spring. The sampling area temperatures ranged from 46° C. to 78° C. The samples were shipped overnight by mail to the laboratory.

Five gram samples were placed in 60 ml serum vials to which were added 20 ml of modified nitrate mineral salts (MNS) medium (Bowman and Sayler, *Biodegradation* 5:1–11 (1994)). The modified MNMS medium contains 2 mN $NaNO_3$, 2 mM phosphate buffer (pH 6.8), 50 $\mu$M $FeCl_3 \cdot 6H_2O$, 50 $\mu$M $MgSO_4 \cdot 7H_2O$, 10 $\mu$g/l d-biotin and 0.5 $\mu$g/l vitamin $B_{12}$ in 1 lite of deionized water. The vials were sealed with TEFLON™ lined serial stoppers. The vials were purged and fed with 3% methane in air and incubated statically in incubators at 50° C., 60° C., 70° C. or 80° C. (The temperature was chosen on basis of the temperature of the original sample at collection.) During incubation, a pellicle was formed at the air/medium interface. After incubation, the pellicle was harvested. The harvested pellicles were combined to provide a single consortium.

After negative staining, the consortium was photographed using a transmission electron microscope (TEM). A culture of the consortium was grown at 55° C. and 150 rpm mixing. After spinning, the cells obtained in the spin were then placed on carbon coated grids, then stained with 2% phosphotungstic acid. The cells were then observed and photographed using a Jeol 1200 EXII TEM at magnification of 20,000 X to 50,000 X. Most of the cells seen were small and ovoid or rod-shaped. Internal membrane disks were seen in many cells. such structures are typical of the II methanotrophs.

Methanotrophs are, in general, slow-growing microorganisms. These thermophilic methanotrophs are very slow growing. Doubling times range from 20 to 30 days under optimum conditions as tested. Greater growth was seen at 60° C. to 70° C. than at 50° C. or 80° C. (methanotrophs previously described grew at temperatures of only up to 45° C.) Hence, the consortium showed unique ability to grow at truly thermophilic temperatures. However, at 70° C. and 80° C. the rates of naphthol production (implying TCE degradation) were much lower. It was also found that adding fresh medium restored the older cultures' soluble methane monooxygenase activity (sMMO) as described below in the examples. This finding implies that deficiencies of the media or inhibitory products may develop with time.

EXAMPLES

Studies were conducted to determine optimum temperature for growth TCE degradation and soluble methane monooxygenase activity (sMMO) for the consortium. The consortium was grown in one-liter side-arm flasks containing 300 ml of modified MNMS medium. The flasks were sealed and purged. The cultures were fed daily with 3% methane in air. Cultures were incubated statically at several different temperatures in water baths at 50° C., 60° C., 70° C. and 80° C. Periodically, the cultures were sampled. The culture growth was determined spectrophotometrically at 600 nm after the sample had cooled to 24° C. in an incubator. To determine the rate of TCE degradation, the rate of naphthol production was determined according to the general method described in Bowman and Sayler (*Biodegradation* 5:1–11 (1994)), except that the assays were performed statically in a water bath at the same temperature at which they were grown.

Biodegradation of TCE by Thermophilic Methanotroph Consortium

Degradation of TCE at thermophilic temperatures was performed using a culture grown on an incubator/shaker obtained from New Brunswick Scientific company, New Brunswick, N.J. Cultures were grown at 55° C. and 150 rpms. After the culture was degassed with compressed air, 5 ml of culture was added to fifteen 60-ml serum bottles. For control, 5 ml of sterile MNMS was added to 60 ml serum bottles. To each bottle was added a solution of TCE so that the final concentration of TCE in the serum bottle was about 0.5 $\mu$g/l. The bottles were inverted and returned to the incubator/shaker. After 5 days of incubation, the TCE concentration was measured and compared.

Thermophilic Growth and Naphthol Production by Shaken Cultures of MNMS and L Medium The cultures were prepared as described above, except that some of the samples contained L medium, which contains 2 g/L $NaNO_3$, 0.2 g/ml $MgSO_4 \cdot 7H_2O$, 0.001 g/l $FeSO_4 \cdot 7H_2O$, 0.21 g/l $Ma_{2PO}4$, 0.09 g/l $NaH_2PO_4$, 0.04 g/l KCl, 0.015 g/l $CaCl_2$ and 1 ml of a stock solution containing, in each 0.1 liter, 0.5 mg $CuSO_4 \cdot 5H_2O$, 1 mg $H_3BO_3$, 1 mg $MnSO_4 \cdot 7H_2O$, 7 mg $ZnSO_4 \cdot 7H_2O$ and 1 mg $MoO_3$. The cultures were shaken at 150 rpm in an incubator/shaker held at 55° C. Growth and 1-naphthol production were measured as described above. Naphthol production assays were performed on the same shaker at 55° C.

As a result of the testing, it was found that optimum temperature for TCE degradation (as inferred from the sMMO activity data) appears to be between 50° C. and 60° C. Since results with the thermophilic consortium were obtained using statically grown cultures, cultures containing the consortium were grown at 55° C. with active mixing and similarly tested. Growth and sMMO activity were compared for cultures of thermophilic methanotroph consortium growth in L and MNMS media. It was found that the thermophilic consortium grows better in MNMS than in the L medium. If the growth rate with rapid mixing and with static growth are compared, the growth rate is seen to nearly double with mixing. Because the methane and oxygen have lower solubilities in aqueous environments at high temperatures, the rapid mixing may increase the residence time of these gases in the medium.

Cells grown in the two media also showed very different sMMO activities. There was no activity when cells were grown in L medium. The L medium contains copper, and lack of activity may be due to inhibitory activity of copper on the medium. (Typical Type II methanotrophs are known to be copper-sensitive.)

Rate of Naphthol Production With No Methane Additions

The culture used above was tested for stability of the soluble methane monooxygenase activity (sMMO) after methane addition was stopped. After the culture was degassed, the culture flask was resealed and returned to the incubator/shaker, but no methane was added. Each day the sMMO activity was measured as described above. It was observed that the sMMO activity increases for two days, then declines if no methane is added. Hence, if this consortium is used in a remediation zone, it is beneficial to replace or rejuvenate by addition of methane after two days. Rejuvenation could be produced by injection of methane into the RZ at appropriate intervals. (When using the consortium in fermentation processes, the addition of methane, if methane is not a product of the process, should be considered. However, because many industrial fermentation processes result in production of methane, addition of methane may not be required.)

Consortium of sMMO Activity When Cells Are Immobilized on ISOLITE™

Study of rates of sMMO activity were accomplished using consortium cells immobilized on ISOLITE™, which is a diatomaceous earth product (78% $SiO_2$, 12% $Al_2O_3$ and 5% $Fe_2O_3$) which is used to immobilize cells and for soil aeration. This is an inert material with no adsorption capacity for TCE. The ISOLITE™ was prewashed in deionized water to eliminate dust, then dried in an oven at 120° C. for 48 hours. Three hundred ml samples of 20 day-old consortium in MNMS media were added to 150 grams of ISOLITE™ in a flask. The flask was placed on an incubator/shaker (20 rpm at 55° C.) for two weeks to allow the cells to bind to the ISOLITE™. The aqueous phase was then removed from the ISOLITE™. One gram of this inoculated material was then used in the assay measuring naphthol production from naphthalene.

When the inoculated ISOLITE™ was used, it was found that the immobilized cells of the consortium produced 1-naphthol from naphthalene in the sMMO assay at a rate of 10 $\mu$m/h/g of ISOLITE™.

The above would indicate that these immobilized cells may be used to degrade TCE in soils. ISOLITE™ does not absorb TCE and could not capture TCE. Hence, if ISOLITE™ were used in the RZ the TCE could be moved back and forth through the RZ until biodegradation was achieved simply by changing the polarity of electrodes placed in the material subject to remediation.

TCE degradation using the thermophilic consortium was tested using an early growth state of culture in the presence of TCE. This was a culture grown at 55° C. and shaken at 150 rpm. Controls for the experiment contained only MNMS medium and added TCE. After five days of incubation at 55° C., the TCE concentration measurements showed significant degradation of TCE in the vials with thermophilic methanotrophs. The controls averaged 0.47

μg/l TCE and the treated vials averaged 0.03 μg/l. Thus, a 94% reduction in the TCE concentration occurred. Results show that the degradation by the thermophiles was significantly different from the controls at the 0.05 alpha level, using a one-way analysis of the variance test.

Consortia of the invention may also be used in biofilters for degradation of industrial wastes, including both liquid and volatile wastes.

As taught herein, the consortium gives rise to monooxygenase. Moreover, from the consortium it is possible to obtain, by methods of the prior art, other cellular enzymes including proteases, DNA polymerases, lipases, cellulases, etc.

What we claim is:

1. A consortium of methanotrophs which show optimal growth at 50° C. to 80° and which degrade trichloroethylene and naphthalene after being grown in the presence of methane.
2. A consortium of claim 1 in a composition undergoing fermentation.
3. A consortium of claim 1 in a remediation zone.
4. A consortium of claim 1 in a biofilter.
5. A consortium of claim 1 in a media containing methane.
6. A method of degrading pollutants comprising the steps of:
   1) preparing a composition of claim 1
   2) adding a composition of claim 1 to a composition containing an environmental pollutant,
   3) allowing the composition obtained in step 2 to grow at a temperature of at least 50° C. to degrade pollutants.
7. A method of claim 6 wherein the composition containing the pollutant is in a remediation zone.
8. A method of claim 7 wherein methane is added to the remediation zone to encourage growth.
9. A consortium of claim 1 wherein the optimum growth is achieved at between 50° C. and 60° C.
10. A composition of matter comprising a consortium of claim 1 in growth media.
11. A composition of claim 10 wherein the growth medium contains methane.
12. A composition of claim 11 wherein the methane is present in the medium at a concentration of about 3%.
13. A consortium of claim 1 wherein the concentration of methane in said media is about 3%.
14. A method of producing enzymes by culturing the consortium of claim 1.
15. A method of claim 14 wherein the enzymes produced is at least one of proteases, DNA polymerases, lipases, cellulases.
16. A method of claim 14 wherein the enzyme produced is monooxygenase.
17. A method of claim 7 wherein the degradation takes place by a process of oxidation and the temperature is above 50° C.
18. A method of claim 17 wherein the compounds oxidized are alkanes, alcohols or halogenated compounds.

* * * * *